United States Patent
Gentry et al.

(10) Patent No.: US 9,222,114 B1
(45) Date of Patent: Dec. 29, 2015

(54) THERMOPHILIC PHOSPHATASES AND METHODS FOR PROCESSING STARCH USING THE SAME

(71) Applicant: University of Kentucky Research Foundation, Lexington, KY (US)

(72) Inventors: Matthew Gentry, Lexington, KY (US); Craig Vander Kooi, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/282,815

(22) Filed: May 20, 2014

Related U.S. Application Data

(60) Provisional application No. 61/825,440, filed on May 20, 2013.

(51) Int. Cl.
*C12P 19/00* (2006.01)
*C12N 9/16* (2006.01)

(52) U.S. Cl.
CPC .. *C12P 19/00* (2013.01); *C12N 9/16* (2013.01)

(58) Field of Classification Search
None
See application file for complete search history.

(56) References Cited

PUBLICATIONS

"A 100%-complete sequence reveals unusually simple genomic features in the hot-spring red alga Cyanidioschyzon merolae" BMC Biol. 5:28-28(2007).*
Edner, et al, "Glucan, Water Dinkinase Activity Stimulates Breakdown of Starch Granules by Plastidial β-Amylases", Plant Physiology, vol. 145, Sep. 2007, pp. 17-28.
Gentry, et al, "The phosphatase laforin crosses evolutionary boundaries and links carbohydrate metabolism to neuronal disease", JCB, vol. 178, No. 3, Jul. 30, 2007, pp. 477-488.
Haki, et al, "Developments in industrial important thermostable enzymes: a review", Bioresource Technology, vol. 89, 2003, pp. 17-34.
Jobling, Steve, "Improving starch for food and industrial applications", Current Opinion in Plant Biology, vol. 7, 2004, pp. 210-218.
Kelly, et al, "Stach and α-glucan acting enzymes, modulating their properties by directed evolution", Journal of Biotechnology, vol. 140, 2009, pp. 184-193.
Kotting, et al, "STARCH-EXCESS4 Is a Laforin-Like Phosphoglucan Phosphatase Required for Starch Degradation in Arabidopsis thaliana", The Plant Cell, vol. 21, Jan. 2009, pp. 334-346.
Leemhuis, et al, "Engineering of cyclodextrin glucanotransferases and the impact for biotechnical applications", Appl Microbiol Biotechnol, vol. 85, 2010, pp. 823-835.
Leslie, Mitch, "Catching killer carbs", JCB, vol. 178, No. 3, 2007, pp. 338-339.
Morell, et al, "Towards the rational design of cereal starches", Current Opinion in Plant Biology, vol. 8, 2005, pp. 204-210.
Nielsen, et al, "Protein engineering of bacterial α-amylases", Biochimica et Biophysica Acta, vol. 1543, 2000, pp. 253-274.
Sanchez, et al, "Trends in biotechnological production of fuel ethanol from different feedstocks", Bioresource Technology, vol. 99, 2008, pp. 5270-5295.
Santelia, et al, "Progress in Arabidopsis starch research and potential biotechnological applications", Current Opinion in Biotechnology, vol. 22, 2010, pp. 1-10.
Sherwood, et al., A malachite green-based assay to assess glucan phosphatase activity. Analyical Biochemistry, vol. 435, 2013, pp. 54-56.
Vander Kooi, et al, "Structural basis for the glucan phosphatase activity of Starch Excess4", PNAS, vol. 107, pp. 15379-84.
Wang, et al, "Glycogen and related polysaccharides inhibit the laforin dual-specificity protein phosphatase." Biochemical and Biophysical Research Communications, vol. 325, 2004, pp. 726-730.
Meekins, et al, "Phosphoglucan-bound structure of starch phosphatase Starch Excess4 reveals the mechanism for C6 specificity," PNAS Early Edition, 2014; pp. 1-6.

* cited by examiner

*Primary Examiner* — Suzanne M Noakes
*Assistant Examiner* — Jae W Lee
(74) *Attorney, Agent, or Firm* — Stites & Harbison PLLC; Mandy Wilson Decker

(57) ABSTRACT

The presently-disclosed subject matter includes thermophilic glucan phosphatase polypeptides. In some embodiments the polypeptide includes non-native laforin polypeptides, or fragments and/or variants thereof, and in some instances the polypeptide can alter the biophysical properties of starch in vitro or in planta. The presently-disclosed subject matter also includes isolated polynucleotides encoding the present polypeptides, methods for processing starch by exposing starch to the present polypeptides, and methods for making the present polypeptides.

6 Claims, 7 Drawing Sheets

THERMOPHILIC PHOSPHATASES AND METHODS FOR PROCESSING STARCH USING THE SAME

RELATED APPLICATION

This application claims priority from U.S. Provisional Patent Application No. 61/825,440, filed May 20, 2013, the entire disclosure of which is incorporated herein by this reference.

GOVERNMENT INTEREST

This invention was made with government support under Grant Number R01NS070899 awarded the National Institutes of Health and Grant Number MCB1252345 awarded by the National Science Foundation. The government has certain rights in the invention.

TECHNICAL FIELD

The presently-disclosed subject matter relates to proteins such as glucan phosphatases and methods of using the same to process starch. In particular, embodiments of the presently-disclosed subject matter relate to thermophilic phosphatase as well as methods for processing starch utilizing at least a thermophilic phosphatase and an amylase.

INTRODUCTION

Starch is an important compound for many different purposes, including for food sources, beverages, the manufacture of plastics, energy sources such as biofuels, industrial feedstocks, and so forth. For instance, starch from the seeds of cereal crops and the tubers of potatoes and cassava accounts for 50-80% of daily caloric intake. In the United States, over 20% of corn starch is converted into ethanol for use as a renewable biofuel, and starch also plays a central role in the production of molecular hydrogen by some micro algae and in algal oil production. Microalgal oil production is increased by supplying starch to the microalgae so that they grow mixotrophically rather than autotrophically. Starch is also a cheap and renewable industrial feedstock for producing paper, textiles, adhesives, plastics, and pharmaceuticals.

Starch is comprised of amylose and amylopectin, which are both glucose polymers. Amylose, the minor component, is a linear molecule comprised of glucose moieties linked together by α-1,4-glycosidic bonds with very few branches. Amylopectin, the major component, is comprised of glucose linked together by α-1,4-glycosidic bonds with α-1,6-glycosidic branches occurring every 12-25 glucose moieties. The branches in amylopectin are arranged in clusters at regular intervals, resulting in a tree-like pattern. Within the clusters, adjacent glucose chains form double helices and the clusters organize into crystalline lamellae. The crystalline lamellae make amylopectin, and thus starch, water-insoluble. This insolubility renders the surface of starch inaccessible to most enzymes, including the amylases that can break it down for processing. The structures of amylopectin (1) and amylase (2) are shown below.

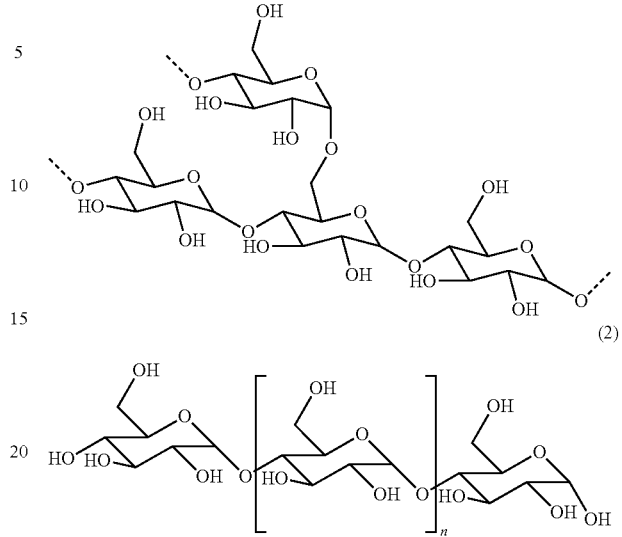

Therefore, to utilize starch for subsequent processing, starch-based feedstocks are generated by a three-phase approach that utilizes physical, chemical, and enzymatic modification (FIG. 1). The physical modification produces high energy costs due to both milling the material and cyclically modulating the temperature between 50° C. to over 100° C. to liquefy starch. In addition to physical modification, large amounts of acids and bases are utilized to increase enzymatic accessibility. Large quantities of these chemicals are costly to purchase and companies also incur the cost of disposing the hazardous waste. Finally, these processes require relatively large amounts of recombinant α-amylase, which cleave α-1,4-glycosidic linkages, to convert the complex sugar into fermentable glucose in these.

Over the last 25 years others have attempted to optimize α-amylase catalytic efficiency, thermostability, and pH tolerance to increase starch processing techniques. These efforts utilize a three-tiered approach of exploiting α-amylases' biological diversity, structure/function analysis, and directed evolution. Despite advances in increased catalytic efficiency as well as heat and pH tolerance, the amylases are still unable to degrade starch without mechanical and chemical assistance. Thus, generating starch-feedstocks using known techniques still results in high costs and environmental concerns related to feedstock chemical treatments.

Hence, there remains a need for compositions and methods for processing starch that are relatively less expensive, more efficient, and present fewer environmental concerns than known compositions and methods.

BRIEF DESCRIPTION OF THE SEQUENCE LISTING

The following is a brief description of the Sequence Listing that is attached hereto and is hereby incorporated by reference in its entirety.

SEQ ID NO: 1 is a nucleic acid sequence encoding a *Cyanidioschyzon merolae* laforin polypeptide of SEQ ID NO: 2;

SEQ ID NO: 2 is an amino acid sequence encoding a *Cyanidioschyzon merolae* laforin polypeptide;

SEQ ID NO: 3 is a nucleic acid sequence encoding a *Cyanidioschyzon merolae* laforin polypeptide fragment of SEQ ID NO: 4;

SEQ ID NO: 4 is an amino acid sequence encoding a *Cyanidioschyzon merolae* laforin polypeptide fragment.

SEQ ID NO: 5 is a nucleic acid sequence encoding a *Cyanidioschyzon merolae* laforin polypeptide fragment of SEQ ID NO: 6;

SEQ ID NO: 6 is an amino acid sequence encoding a *Cyanidioschyzon merolae* laforin polypeptide fragment.

SEQ ID NO: 7 is a nucleic acid sequence encoding a *Cyanidioschyzon merolae* laforin polypeptide fragment of SEQ ID NO: 8;

SEQ ID NO: 8 is an amino acid sequence encoding a *Cyanidioschyzon merolae* laforin polypeptide fragment.

SEQ ID NO: 9 is a nucleic acid sequence encoding a *Cyanidioschyzon merolae* laforin polypeptide fragment of SEQ ID NO: 10;

SEQ ID NO: 10 is an amino acid sequence encoding a *Cyanidioschyzon merolae* laforin polypeptide fragment.

DETAILED DESCRIPTION OF EXEMPLARY EMBODIMENTS

Figure 1:
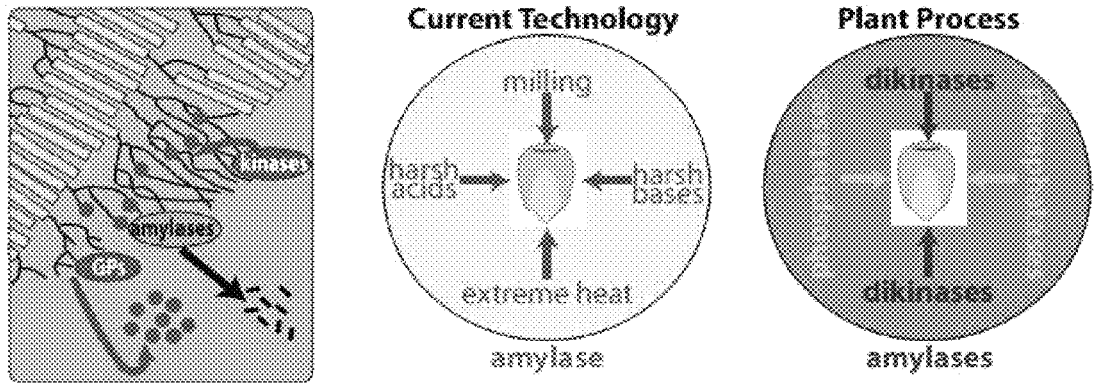
FIG. 1 includes a schematic showing a conventional method for processing starch compared to a plant-based starch processing method.
Figure 2:
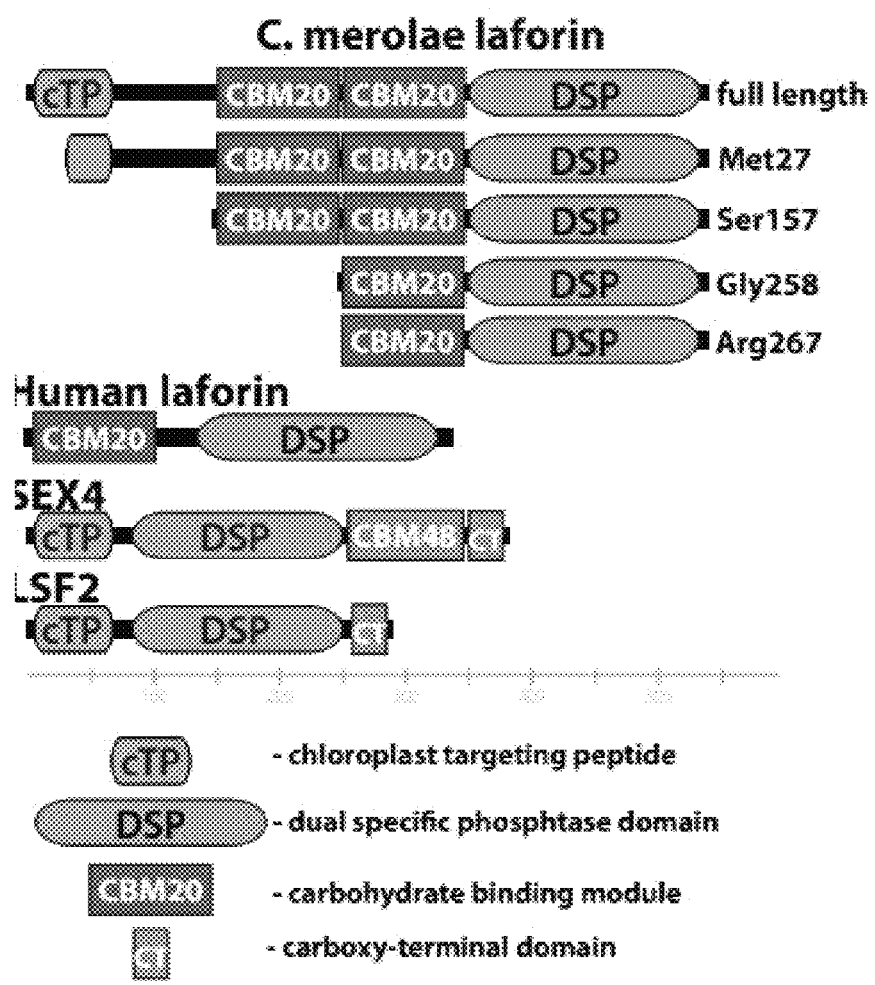
FIG. 2 includes a schematic showing the sequences of the phosphatases of SEQ ID NOS: 2, 4, 6, 8, and 10 as well as human laforin, SEX4, and LSF2.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The present invention relates to novel, unique enzymes (i.e., polypeptides) for processing starch. Processing starch can include physically modifying the structure of a starch, and in certain instances includes degrading the starch. The polypeptides disclosed herein can also alter the biophysical properties of starch and/or total biomass starch production. For example, some embodiments of the present polypeptides can increase total biomass starch production and/or degrade starch in vitro, in planta, or both.

As used herein, the term "starch" is given its ordinary meaning in the art. In this regard, starches are heterogeneous, and their physicochemical properties, composition with respect to amylose versus amylopectin, amount of phosphorylation, and molecular structure all can vary greatly depending on the source of the starch. These properties can also affect starch gelatinization and viscosity, and thus impact starch processing. Exemplary starch sources include, but are not limited to, *Arabidopsis*, potato, corn, cassava, rice, wheat, and the like.

As used herein, the terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

In some embodiments the presently-disclosed polypeptides include thermophilic phosphatases and/or thermophilic glucan phosphatases. Glucan phosphatases dephosphorylate glucans in starch metabolism. In some instances, glucan phosphatases dephosphorylate glucans so that starch can be completely degraded by amylases.

In some embodiments the polypeptide is a laforin polypeptide, or a fragment and/or variant thereof. In some embodiments the laforin polypeptide can be a vertebrate laforin or a vertebrate laforin ortholog. Exemplary vertebrate laforin orthologs can include about 85%, about 90%, or about 95% similarity with other vertebrate laforin at the amino acid level. Furthermore, in some embodiments the polypeptide includes a protozoan laforin, or a fragment and/or variant thereof. The laforin can be based on laforin obtained from protozoa including, but not limited to, *tetrahymena thermophile, Eimeria tenella, Toxoplasma gondii, Paramecium tetraurelia, Neospora caninum*, and *Cyanidioschyzon merolae*. Exemplary protozoan laforin orthologs can include about 20% or more, about 25% or more, about 30% or more, or about 35% or more similarity with *Homo sapien* laforin (Hs-laforin) at the amino acid level.

Certain plant species, such as single-cell algae *Cyanidioschyzon merolae* (*C. merolae*), include thermophilic polypeptides (thermophile) that can process and degrade native starch under harsh temperatures and extreme pH conditions in. For instance, *C. merolae* lives in acidic environments at temperatures of about 50 to about 75° C., living in and around thermal vents. The present inventors have found that *C. merolae* includes laforin (hereinafter "Cm-laforin") polypeptides that can enhance starch degradation by amylases and allow amylases to release more glucose. A full length native wild-type protein sequence for Cm-laforin is included herein (SEQ ID NO: 2). Embodiments of the presently-disclosed polypeptides include isolated and/or non-naturally occurring fragments and/or variants of wild-type laforin.

Accordingly, in some embodiments the polypeptide is a thermophile. The term "thermophile" herein refers to characteristic of operating normally (i.e., is stable) at least at temperatures above about 40° C. In some embodiments the thermophile can operate at temperatures between about 40° C. and about 85° C. For example, a "thermophilic polypeptide," "thermophile," or and the like refer to a polypeptide that can function at least at temperatures above about 40° C., and a "thermophilic organism" is an organism that can function at least at temperatures above about 40° C. Some thermophiles can also be stable at relatively lower temperatures. For instance, some exemplary Cm-laforin polypeptides are stable at temperatures of about 10° C. to about 75° C.

Additionally, in some embodiments the polypeptide can be stable at non-neutral pH. In some embodiments the polypeptide can be stable at about 3.0 pH to about 8.0 pH. In specific embodiments the polypeptide can be stable at about 3.0 pH, 4.0 pH, 5.0 pH, 6.0 pH, 7.0 pH, or 8.0 pH.

In some embodiments the polypeptide is a fragment of the polypeptide including the sequence of SEQ ID NO: 2. The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus, carboxy-terminus of the reference polypeptide, or alternatively both. A fragment can also be a "functional fragment," in which case the fragment retains some or all of the activity of the reference polypeptide as described herein.

In some embodiments the polypeptide can comprise the sequence of SEQ ID NO: 2 and can include about 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, or 531 amino acid residues. In specific embodiments the polypeptide fragments include about 1 to about 266 amino acid residues deleted from the N-terminus of the polypeptide, including polypeptide fragments having about 1 to about 266 amino acid residues deleted from the N-terminus immediately following the start methionine (M) amino acid.

As described herein, the presently disclosed subject matter also include variants of the presently-disclosed polypeptides. The term "variant" refers to an amino acid sequence that is different from the reference polypeptide by one or more amino acids, e.g., one or more amino acid substitutions. For example a glucan phosphate polypeptide variant differs from wild-type glucan phosphatase by one or more amino acid substitutions, i.e., mutations. In this regard, polypeptide variants comprising combinations of two or more mutations can respectively be referred to as double mutants, triple mutants, and so forth. It will be recognized that certain mutations can result in a notable change in function of a polypeptide, while other mutations will result in little to no notable change in function of the polypeptide.

In some embodiment the present polypeptides include constituents that share at least 75% homology with a wild type polypeptide. In some embodiments the polypeptides share at least 85% homology with the wild type polypeptide. In some embodiments the polypeptides share at least 90% homology with the wild type polypeptide. In some embodiments the polypeptides share at least 95% homology with the wild type polypeptide. The wild type polypeptide can include the non-native Cm-laforin polypeptide having the sequence of SEQ ID NO: 2.

"Percent identity," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). [BLAST nucleotide searches are performed with the NBLAST program, score+100, wordlength=12, to obtain nucleotide sequences homologous to a nucleic acid molecule of the invention. BLAST protein searches are performed with the XBLAST program, score=50, word length=3, to obtain amino acid sequences homologous to a reference polypeptide (e.g., SEQ ID NO: X). To obtain gapped alignments for comparison purposes, Gapped BLAST is utilized as described in Altschul, et al. (Nucleic Acids Res. 25: 3389-3402, 1997). When utilizing BLAST and Gapped BLAST programs, the default parameters of the respective programs (e.g., XBLAST and NBLAST) are used. See http://www.ncbi.nlm.nik.gov, and reference is made to the most recent version of the programs that are available as of Jul. 19, 2012.

In one embodiment the polypeptide comprises the sequence of SEQ ID NO: 4. In another embodiment the polypeptide comprises a fragment, a variant, or both a fragment and variant of SEQ ID NO: 4. In another embodiment the polypeptide comprises the sequence of SEQ ID NO: 6. In another embodiment the polypeptide comprises a fragment, a variant, or both a fragment and variant of SEQ ID NO: 6. In another embodiment the polypeptide comprises the sequence of SEQ ID NO: 8. In another embodiment the polypeptide comprises a fragment, a variant, or both a fragment and variant of SEQ ID NO: 8. In another embodiment the polypeptide comprises the sequence of SEQ ID NO: 10. In another embodiment the polypeptide comprises a fragment, a variant, or both a fragment and variant of SEQ ID NO: 10.

The presently-disclosed subject matter also includes isolated polynucleotides that encode any of the presently-disclosed polypeptides. The terms "nucleotide," "polynucleotide," "nucleic acid," and "nucleic acid sequence" refer to deoxyribonucleotides or ribonucleotides and polymers thereof in either single or double stranded form. Unless specifically limited, the term encompasses nucleic acids containing known analogues of natural nucleotides that have similar binding properties as the reference nucleic acid and are metabolized in a manner similar to naturally occurring nucleotides. The terms also include compounds only comprising the coding regions, or exons, of a particular DNA sequence. The terms are therefore inclusive of cDNA molecules.

The term "isolated", when used in the context of an isolated polynucleotide or an isolated polypeptide, is a polynucleotide or polypeptide that, by the hand of man, exists apart from its native environment and is therefore not a product of nature. An isolated polynucleotide or polypeptide can exist in a purified form or can exist in a non-native environment such as, for example, in a transgenic host cell. Unless otherwise indicated, all polypeptides and polynucleotides described herein include isolated forms thereof even where not explicitly recited. Thus, unless stated otherwise, all the polypeptide and polynucleotide described herein can be modified by the term isolated.

In some embodiments the polynucleotides encode a thermophilic phosphatase, laforin polypeptide, and/or a Cm-laforin polypeptide. In other embodiments the polynucleotide includes the sequence of SEQ ID NO: 1, and the polynucleotide encodes the polypeptide including the sequence of SEQ ID NO: 2. In other embodiments the polynucleotide encodes a fragment and/or a variant of the polypeptide including the sequence of SEQ ID NO: 2.

As before, the term "polynucleotide fragment" or the like can refer to a polynucleotide in which nucleic acids are deleted as compared to the reference polynucleotide itself, but where the remaining nucleic acid sequence is usually identical to the corresponding positions in the reference polynucleotide. Such deletions can occur at any location of the sequence. In some embodiments the polynucleotide includes a fragment of the isolated polynucleotide having the sequence of SEQ ID NO: 1. In some embodiments the polynucleotide fragment includes about 800, 900, 1000, 1100, 1200, 1300, 1400, 1500, or more nucleotides, and in some embodiments the polynucleotide fragment includes about 801 to about 1596 nucleotides.

The term "variant" in reference to a polynucleotide can refer to a polynucleotide that is different from the reference polynucleotide by one or more nucleic acids. In this regard, some polynucleotide variants have been codon optimized relative to a reference polynucleotide, and the polynucleotide variant can produce polypeptide more effectively in certain organisms relative to the reference polynucleotide. For instance, in some embodiments a polynucleotide that includes the sequence of SEQ ID NOS: 3, 4, 5, or 9 expresses, respectively, a polypeptide that includes the sequence of SEQ ID NOS: 4, 6, 8, or 10 more effectively (e.g., higher purity) in *E. coli* cells when compared to the polynucleotide having the sequence of SEQ ID NO: 1. In this respect, a polynucleotide variant can have a different sequence than a reference polynucleotide without necessarily expressing a polypeptide that includes amino acid mutations relative to the reference polypeptide.

Unless otherwise indicated, a particular nucleic acid sequence also implicitly encompasses conservatively modified versions thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al. (1991) Nucleic Acid Res 19:5081; Ohtsuka et al. (1985) J Biol Chem 260:2605 2608; Rossolini et al. (1994) Mol Cell Probes 8:91 98). Thus, the term polynucleotide includes both deoxyribonucleic acid (DNA) and ribonucleic acid, and therefore the term polynucleotide specifically includes complementary DNA as used herein.

In some embodiments the polynucleotide includes the nucleotide sequence of SEQ ID NO: 3. In some embodiments the polynucleotide includes the nucleotide sequence of SEQ ID NO: 5. In some embodiments the polynucleotide includes the nucleotide sequence of SEQ ID NO: 7. In some embodiments the polynucleotide includes the nucleotide sequence of SEQ ID NO: 9.

The presently-disclosed subject matter further includes a composition comprising starch, wherein the starch is from a plant expressing one of the polypeptides described herein. In some embodiments the polypeptide includes a thermophilic glucan phosphatase polypeptide. In some embodiments the polypeptides includes a laforin polypeptide, such as a Cm-laforin polypeptide. As discussed herein, organisms expressing the present polypeptides can produce starch with altered biophysical properties, which can be beneficial for manufacturing processes in various industries, including food, beverage, confectionary, plastic, paper, building, energy, textile, agriculture, and pharmaceutical industries.

The presently-disclosed subject matter further includes methods for processing starch, wherein processing can include degrading starch to smaller polysaccharides and/or monosaccharides. In some embodiments the methods for processing starch comprise providing a starch, exposing the starch to a thermophilic glucan phosphatase, and collecting the starch that has been exposed to the thermophilic glucan phosphatase. In some embodiments the present polypeptides can be used in a method for processing starch that does not require harsh acids and harsh bases. Thus, the present methods can be more cost-effective and have a smaller environmental impact relative to known methods.

The term "providing" as used herein to refer to delivering, obtaining, procuring, or the like a substance. For instance, a polypeptide, a starch, or both can be provided by any means. In some embodiments the polypeptide is provided in an isolated form that can be exposed directly to a starch. In other embodiments an organism expresses the polypeptide, and the polypeptide is thereby provided by the organism. Likewise, starch can be provided by itself or can be provided within a plant.

In some embodiments the exposing step occurs within a plant. That is, a plant can express a thermophilic glucan phosphatase, and the thermophilic glucan phosphatase can be exposed to starch within the plant. On the other hand, in industrial applications a thermophilic glucan phosphatase can be provided in an isolated form, and can be exposed to a starch by mixing the two components in a container.

The term "collecting" is used herein to refer to any process or method where starch is used, obtained, cultivated, ingested, or the like. For example, in some embodiments starch is collected by harvesting a plant that comprises starch and processing the plant in order to obtain starch or other sugars derived therefrom. In some embodiments, collecting refers to ingesting a plant that comprises a thermophilic glucan phosphatase. In other embodiments collecting refers to collecting starch that has been processed in a container with a thermophilic glucan phosphatase.

The presently-described starch processing methods do not suffer from the inability of amylases to access starch's water insoluble surface. Amylases degrade starch to maltose and glucose, but despite industry's 25 years of optimizing amylase to work under extreme conditions, amylase cannot degrade its own starch. In order to solubilize starch and to make it accessible to amylase, milling, extreme heat and acids and bases are required. One recent improved method for processing starch is described in U.S. Provisional patent application Ser. No. 13/928,160, which is incorporated herein by reference, and which describes non-thermophilic glucan phosphatase variants for starch dephosphorylation.

However, in order to overcome problems in the art, the present inventors discovered that use of the present polypeptides allows the starch to be processed without the milling and chemical treatments that are typically required. Thus, in some instances the present polypeptides can make a starch accessible to amylases for processing. The present methods can utilize polypeptides that include a thermophilic glucan phosphatase, such as laforin and the like. In specific embodiments the thermophilic glucan phosphatase includes the sequence of SEQ ID NO: 2, or a fragment and/or variant thereof.

Some methods further comprise exposing the starch to a kinase, an amylase, or both before the collecting step. Some embodied methods comprise a three-step exposing step wherein the starch is sequentially exposed to a thermophilic phosphatase, a kinase, and an amylase. In some embodied methods glucan dikinases phosphorylate the outer starch surface and solubilize the outer surface allowing amylases to bind and degrade starch, and glucan phosphatases release phosphate and reset the cycle so that amylase-directed degradation can continue past the phosphate. Prior to the present method, no known method used a combination of a thermophilic phosphatase, a kinase, and an amylase to process starch. Instead, prior to the present invention, harsh acids and bases were required to process starches. Accordingly, the present methods that use a one or a combination of one or more different polypeptides are superior to prior know methods for processing starch.

In some embodiments of the present methods, the polypeptides are thermophiles and are capable of functioning under extreme conditions. For instance, Cm-laforin maintains its activity from about 37° C. to about 75° C. and under a wide range of pH conditions, including about 3.0 pH to about 8.0 pH. Additionally, Cm-laforin has a relatively high specific activity and is relatively efficient at removing phosphate from the C3 and C6 position of starch compared to human laforin. Lastly, Cm-laforin can increase amylase-directed degradation of starch.

The presently-disclosed subject matter also includes methods for making an isolated polypeptide. In some embodiments the method comprises providing a cell that includes at least one of the presently-described polynucleotides, culturing the cell under conditions that permit the cell to produce a polypeptide encoded by the polynucleotide, and collecting the polypeptide. The cell can naturally include the polynucleotide or the polynucleotide can be introduced to the cell by known methods. For instance, a vector can be utilized to introduce an embodiment of the present polynucleotides to the cell.

The cell is not particularly limited except that it must be capable of producing the polypeptide encoded by the polynucleotide. In some embodiments the polynucleotides can be sequence optimized for the production of a polypeptide in a particular cell, such as E. coli cells. The polypeptide produced by the cell can be collected by known means, thereby providing the isolated polypeptide.

EXAMPLES

The presently-disclosed subject matter is further illustrated by the following specific but non-limiting examples. Some examples are prophetic. Some of the following examples may include compilations of data that are representative of data gathered at various times during the course of development and experimentation related to the presently-disclosed subject matter.

Example 1

This Example describes the identification, cloning strategies, and purification of Cm-laforin polypeptides.

Laforin genes were identified in six protozoan genomes: *Tetrahymena thermophile, Eimeria tenella, Toxoplasma gondii, Paramecium tetraurelia, Neospora caninum*, and *Cyanidioschyzon merolae*. While the vertebrate laforin orthologs are similar, the protozoan laforin orthologs are about 20% to about 35% identical to Hs-laforin. Furthermore, some of these organisms live in extreme environments and likely have enzymes that function under harsh conditions. For example, the single-cell red algae *C. merolae* lives in highly acidic environments (i.e., pH<2) at temperatures of about 45° C. to about 60° C.

Five of the protozoan laforin orthologs were cloned to identify a laforin ortholog that was amenable to in vitro manipulation. To define the optimal constructs for recombinant protein expression, laforin primary sequences were analyzed from multiple species using a similar strategy that was successful for SEX4 (Vander Kooi et al., 2010). The strategy was to predict domain boundaries, secondary structure, regions of disorder, and regions of hydrophobicity for the polypeptides. Based on these data, the full-length laforin gene was cloned as well as multiple fragments (i.e., truncations) that remove the amino- and/or carboxy-terminus of the protein.

Figure 4:
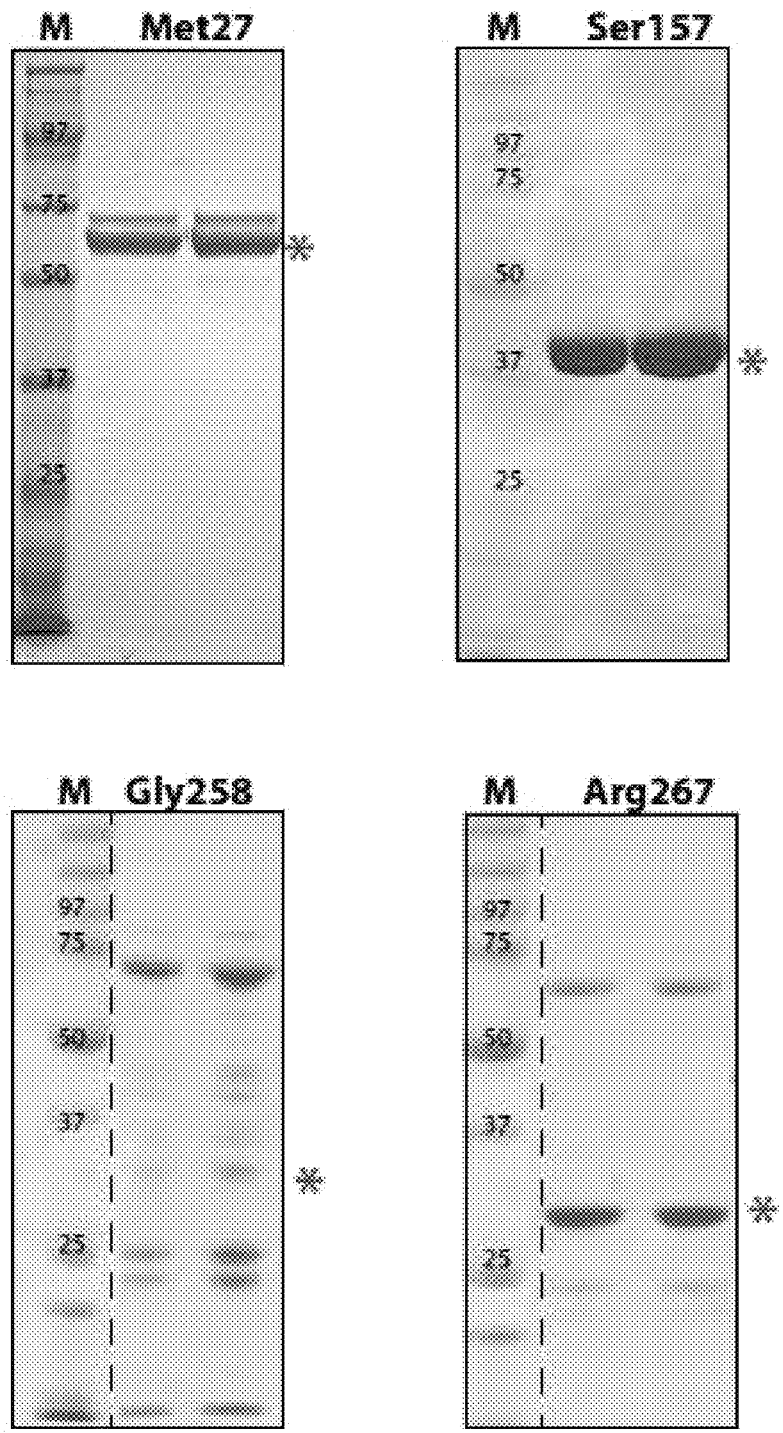
FIG. 4 includes Coomassie stained protein gel images showing the expression and purification of different *C. merolae* laforin (Cm-laforin) fragments from *E. coli*.

In the case of Cm-laforin, thedata, four Cm-laforin fragments were cloned into multiple bacterial expression vectors, including Met27 (truncates first 26 amino acids), a codon optimized for Ser157, a codon optimized for Gly258, and a codon optimized for Arg267. Cm-laforin proteins that were over 99% pure were expressed and purified were produced by tranforming BL21-CodonPlus *Escherichia coli* cells (Stratagene, La Jolla, Calif.) with expression vector. Cells were grown at 37° C. in 2xYT to an O.D.600 of 0.6-0.8, placed in ice for 20 minutes, were induced with 1 mM isopropyl β-D-thiogalactoside (IPTG), were grown at 16° C. for about 16 hours, and were harvested by centrifugation. Cells were lysed in 20 mM Tris-HCl (pH 7.5), 100 mM NaCl, and 2 mM dithiothreitol (DTT), centrifuged, and the proteins were purified using a Profinia IMAC column with Ni2+ beads (Bio-Rad, Hercules, Calif.) with a Profinia protein purification system (Bio-Rad). Polypeptides were eluted in lysis buffer containing 300 mM imidazole. Lastly, polypeptide was purified to homogeneity using a HiLoad 26/60 Superdex 200 size exclusion column (General Electric, Schenectady, N.Y.) (FIG. 4).

About 25 mg of soluble Cm-laforin per liter of *E. coli* cells was purified. The Cm-laforin was capable of being purified to 18 mg/ml, and this polypeptide was stable at 4° C. for over 1 week. Given the relatively high purity that was attained, Cm-laforin was selected for further analysis.

Example 2

This Example describes the cloning and identification of vertebrate laforin orthologs.

A total of seven vertebrate laforin orthologs that all robustly express in *E. coli* were identified, but only enough protein was purified to perform in vitro assays due to protein aggregation and precipitation. The vertebrate laforin orthologs were more than 85% similar at the amino acid level.

To test the glucan phosphatase activity of Cm-laforin, an assay based on the complex formation of malachite green with phospho-molybdate was implemented to measure inorganic phosphate release.

Figure 3:
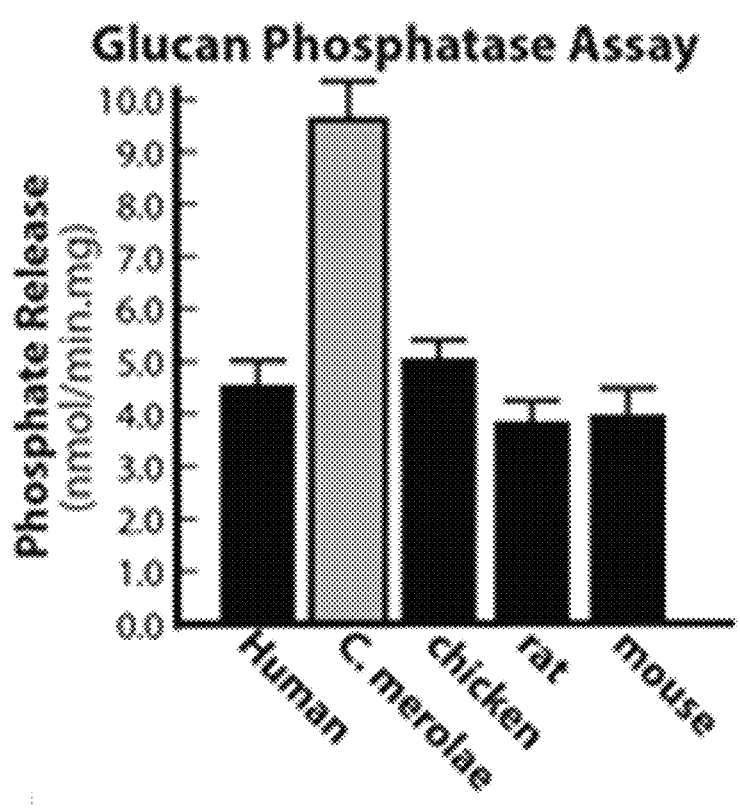
FIG. 3 includes a plot showing the results of a glucan phosphatase assay performed with human, *Cyaniioschyzon merolae* (*C. merolae*), chicken, rat, and mouse laforin.

The glucan phosphatase assays against amylopectin, as determined via released free phosphate by malachite green detection, were performed as previously described with the following modifications (Sherwood, 2013). Reactions were performed in 20 µL, reactions, containing 1× phosphatase buffer (0.1M sodium acetate, 0.05 M bis-Tris, 0.05 M Tris-HCl, pH 7.0, and 2 mM DTT), 100-1000 ng protein, and 45 µg amylopectin. Amylopectin was solubilized using the Roach method (Wang, 2004). The reaction was stopped by the addition of 20 µL, of 100 mM N-ethylmaleamide and 80 µL, of malachite green reagent. Absorbance was measured at 620 m. The assay was performed with each protein six times or more to determine specific activity. Using this assay, it was found that Cm-laforin possessed nearly twice the specific activity of human-laforin, rat-laforin, or mouse-laforin (FIG. 3).

Example 3

This Example describes procedures conducted to characterize the thermophilic activity of Cm-laforin polypeptides.

To observe generic phosphatase activity, a phosphatase assay using the exogenous substrate para-nitrophenyl phosphate (pNPP) was implemented. Most DSPs can cleave pNPP, and this cleavage results in a colorimetric change. Since C. merolae is a thermophile, the phopshatase activity of Cm-laforin was observed under a variety of temperatures and pH conditions.

Previously-described phosphatase assays using pNPP were performed with the following modifications (Sherwood, 2013; Gentry, 2007). Hydrolysis of pNPP was performed in 50 µL, reactions, containing 1× phosphatase buffer (0.1M sodium acetate, 0.05 M bis-Tris, 0.05 M Tris-HCl, and 2 mM DTT) at pH 3-8, 50 mM pNPP, and 1 µg of enzyme at 37-75° C. for 15 minutes. The reaction was terminated by the addition of 200 µL of 0.25 M NaOH, and absorbance was measured at 410 nm. The assay was performed with each protein six times or more to determine specific activity.

Figure 5A:
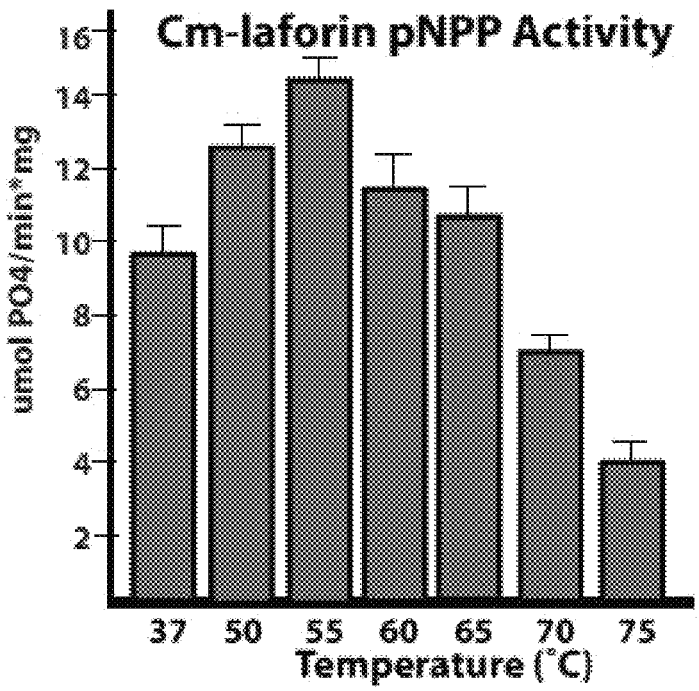
FIG. 5A includes a plot showing Cm-laforin phosphatase activity utilizing a non-biologically relevant substrate pNPP over a range from about 37° C. to about 75° C.
Figure 5B:
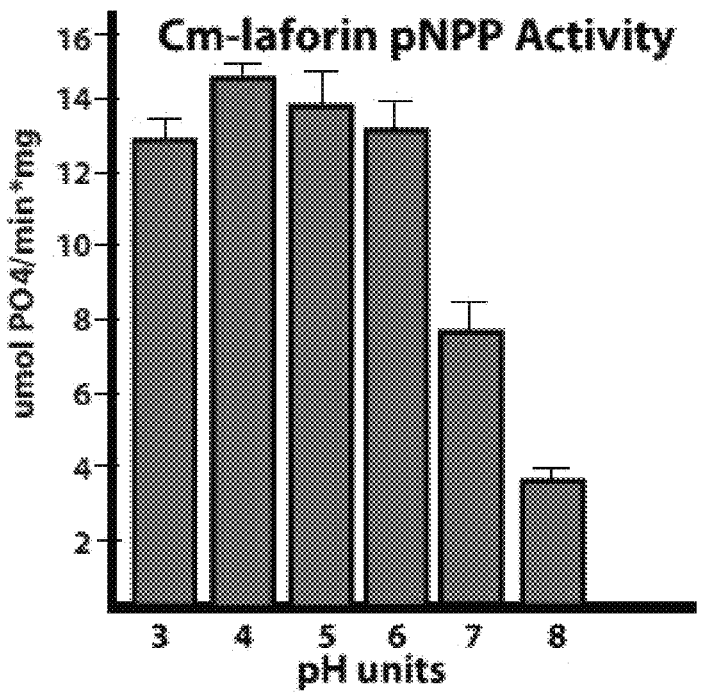
FIG. 5B includes a plot showing Cm-laforin phosphatase activity from about 3.0 pH to about 8.0 pH.
Figure 5C:
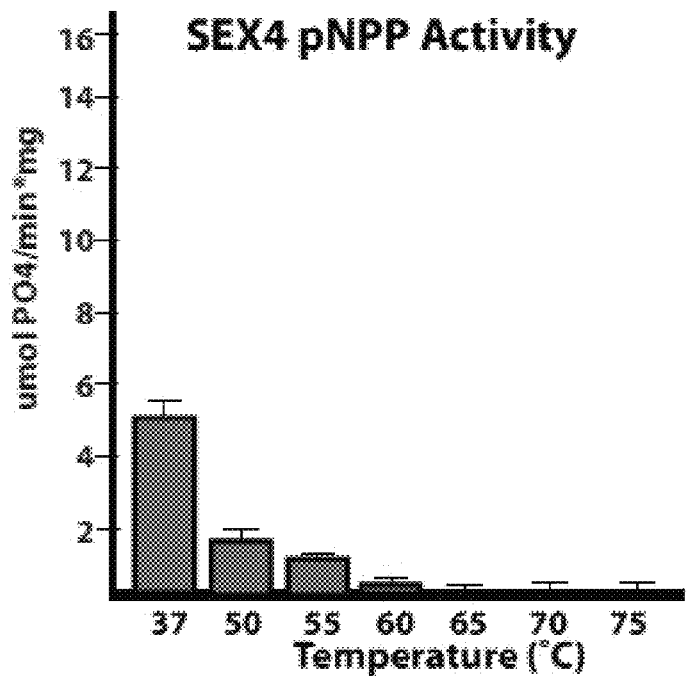
FIG. 5C includes a plot showing SEX phosphatase activity utilizing a non-biologically relevant substrate pNPP over a range from about 37° C. to about 75° C.
Figure 5D:
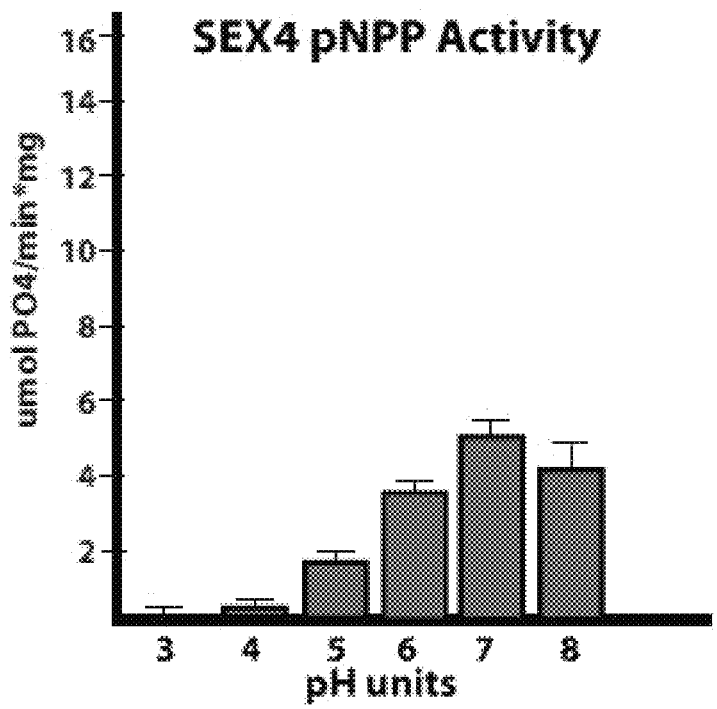
FIG. 5D includes a plot showing SEX4 phosphatase activity from about 3.0 pH to about 8.0 pH.

As shown in FIG. 5A, Cm-laforin maintained its activity from 37° C.-80° C. In addition, Cm-laforin was active over a wide array of pH conditions from about 3.0 pH to about 8.0 pH (FIG. 5B). On the other hand, SEX4 had a significantly lower specific activity against pNPP, and SEX4 did not maintain its activity over a wide-range of temperature or pH conditions (FIGS. 5C and 5D).

Example 4

This Example describes procedures that measured the position of the phosphate that is released off of glucose within starch by Cm-laforin.

Phosphate release from 33P-lableled starch granules was performed as previously described with the following variations (Kotting, 2009). Phosphate-free starch granules were isolated from the *Arabidopsis* sex1-3 mutant. C6-33P-labeleled starch was generated by phosphorylating the starch with $_{33}$P-β-ATP at the C6-position by GWD followed by washing until all unincorporated 33P had been removed, and non-radio-labeled ATP was added with PWD to phosphorylate the C3 position followed by dialyzing and precipitating out the ATP and PWD. C3-33P-labeled starch was generated by phosphorylating the starch with unlabeled ATP at the C6-position by GWD followed by phosphorylation with $_{33}$P-βR-ATP at the C3-position by PWD and washing until all unincorporated 33P had been removed. These products were utilized as substrates in dephosphorylation assays with Cm-laforin or human laforin.

Figure 5E:
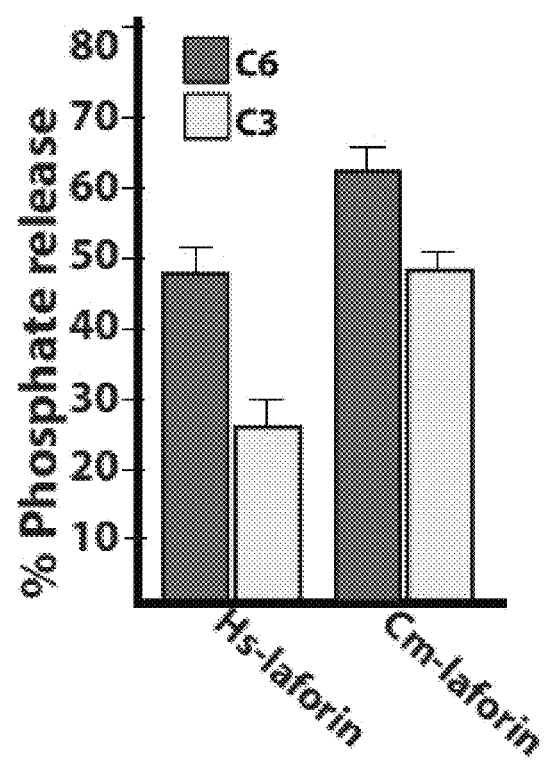
FIG. 5E includes a plot showing the efficiency with which Cm-laforin and Hs-laforin can remove phosphate from the C3 and C6 positions of a glucose ring.

In both the C6-33P- and C3-33P-labeleled cases, the starch granules were phosphorylated at both positions; however, the 33P-label was located at only one or the other position. $_{33}$P-β-ATP was obtained from Hartmann Analytic (Braunschweig, Germany). 150 ng of recombinant proteins were incubated in dephosphorylation buffer (100 mM sodium acetate, 50 mM bis-Tris, 50 mM Tris-HCl, pH 6.5, 0.05% [v/v] Triton X-100, 1 µd/µL [w/v] BSA, and 2 mM DTT) with the C6- or C3-prelabeled starch (4 mg/mL) in a final volume of 150 µL on a rotating wheel for 5 min at 25° C. The reaction was terminated by the addition of 50 µL of 10% SDS. The reaction tubes were then centrifuged at 13,000 rpm for 5 min to pellet the starch. 33P release into 150 µL of supernatant was determined using a 1900 TR liquid scintillation counter (Packard Elmer, Waltham, Mass.). The assay was performed with each protein six times to determine specific activity (FIG. 5E).

Example 5

This Example describes the Cm-laforin's ability to enhance starch degradation to a higher degree than SEX4.

Native *Arabidopsis* starch was treated with combinations of Beta-amylase3 (BAM3) (sweet potato, Sigma A7005, St. Louis, Mo.), isoamylase3 (ISA3) (*Pseudomonas* sp. Sigma 15284), GWD, and SEX4 or Cm-laforin. The total volume of the assays were 200 ul and consisted of 30 mM HEPES-KOH, pH 7.5, 5 mM MgCl$_2$, 5 mM CaCl$_2$, 1 mM ATP, 2.5 mg starch, +/−1 ul stock concentration BAM, +/−1.5 ul 1:50 stock dilution ISA, +/−4.5 ug GWD, +/−4.5 ug SEX4, and +/−4.5 ug laforin. The samples were incubated for 90 minutes with gentle agitation at room temperature. A 1.5 minute spin at 15,000 RPM was performed and the supernatant was collected, followed by another spin at 15,000 RPM for 5 minutes to remove any residual starch. Any remaining oligosaccharides were hydrolyzed, and glucose content in the supernatant was quantified using the Boehringer Mannheim assay kit (10716251035; Ingelheim am Rhein, Germany) per manufacturer's protocol.

Figure 6:
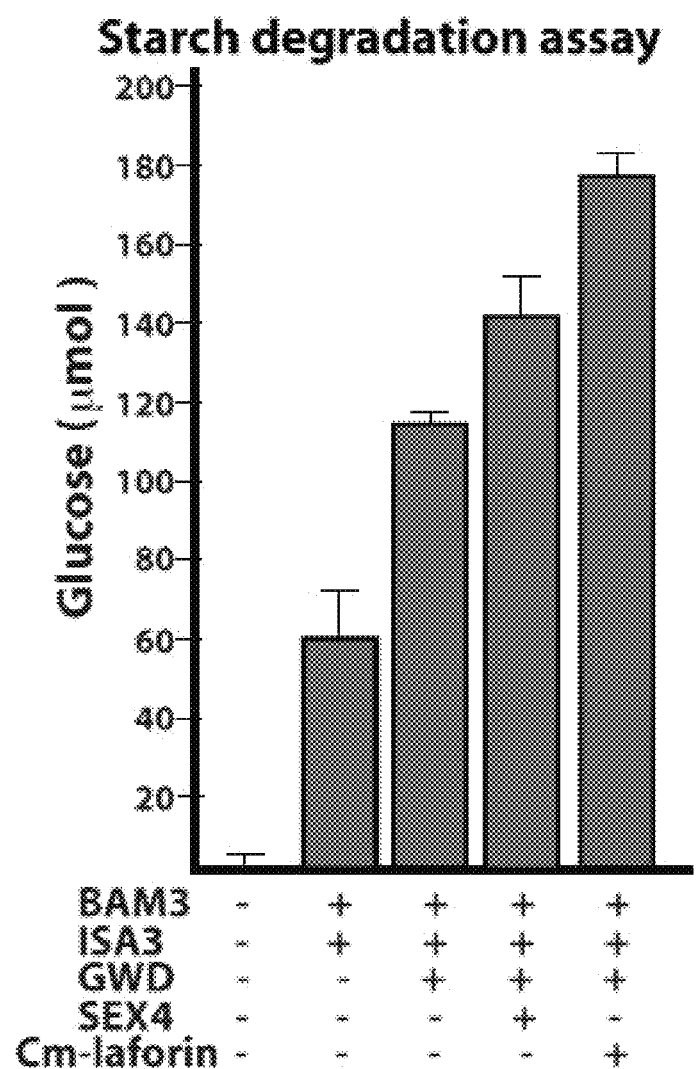
FIG. 6 includes a plot showing that Cm-laforin increases the degradation of starch via amylases (BAM3 and ISA3) in the presence of the kinase GWD.

As shown in FIG. 6, β-amylases (BAM) and isoamylases (ISA) were responsible for degrading starch into glucose and maltose in planta. Phosphate-free starch was isolated from gwd/pwd deficient *Arabidopsis* plants and it was demonstrated that the activity of BAM3 and ISA3 are markedly enhanced in vitro when starch is phosphorylated by the glucan dikinase GWD.

Furthermore, the hydrolysis activity of BAMs and ISA in combination with GWD was observed in the presence and absence of SEX4 and Cm-laforin. The activity of BAM3 and ISA3 increased in the presence of SEX4, and increased further in the presence of Cm-laforin (FIG. 6).

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references, including those listed below, are incorporated herein by reference.

REFERENCES

1. EDNER, et al, "Glucan, Water Dinkinase Activity Stimulates Breakdown of Starch Granules by Plastidial β-Amylases", Plant Physiology, vol. 145, September 2007, pages 17-28.
2. GENTRY, et al, "The phosphatase laforin crosses evolutionary boundaries and links carbohydrate metabolism to neuronal disease", JCB, vol. 178, no. 3, Jul. 30, 2007, pages 477-488.
3. HAKI, et al, "Developments in industrial important thermostable enzymes: a review", Bioresource Technology, vol. 89, 2003, pages 17-34.
4. JOBLING, Steve, "Improving starch for food and industrial applications", Current Opinion in Plant Biology, vol. 7, 2004, pages 210-218.
5. KELLY, et al, "Stach and α-glucan acting enzymes, modulating their properties by directed evolution", Journal of Biotechnology, vol. 140, 2009, pages 184-193.
6. KOTTING, et al, "STARCH-EXCESS4 Is a Laforin-Like Phosphoglucan Phosphatase Required for Starch Degradation in *Arabidopsis thaliana*", The Plant Cell, vol. 21, January 2009, pages 334-346.
7. LEEMHUIS, et al, "Engineering of cyclodextrin glucanotransferases and the impact for biotechnical applications", Appl Microbiol Biotechnol, vol. 85, 2010, pages 823-835.
8. LESLIE, Mitch, "Catching killer carbs", JCB, vol. 178, no. 3, 2007, pages 338-339.
9. MORELL, et al, "Towards the rational design of cereal starches", Current Opinion in Plant Biology, vol. 8, 2005, pages 204-210.
10. NIELSEN, et al, "Protein engineering of bacterial α-amylases", Biochimica et Biophysica Acta, vol. 1543, 2000, pages 253-274.
11. SANCHEZ, et al, "Trends in biotechnological production of fuel ethanol from different feedstocks", Bioresource Technology, vol. 99, 2008, pages 5270-5295.
12. SANTELIA, et al, "Progress in *Arabidopsis* starch research and potential biotechnological applications", Current Opinion in Biotechnology, vol. 22, 2010, pages 1-10.
13. SHERWOOD, et al, A malachite green-based assay to assess glucan phosphatase activity." Analyical Biochemistry, vol. 435, 2013, pages 54-56.
14. VANDER KOOI, et al, "Structural basis for the glucan phosphatase activity of Starch Excess4", PNAS, vol. 107, pages 15379-84.
15. WANG, et al, "Glycogen and related polysaccharides inhibit the laforin dual-specificity protein phosphatase." Biochemical and Biophysical Research Communications, vol. 325, 2004, pages 726-730.

What is claimed is:

1. A non-native glucan phosphatase polypeptide comprising the amino acid sequence as set forth in SEQ ID NO: 6, 8 or 10.

2. The polypeptide of claim 1, wherein the polypeptide is a thermophile.

3. The polypeptide of claim 2, wherein the polypeptide is stable at least at a 3.0 pH to about 8.0 pH.

4. The polypeptide of claim 2, wherein the polypeptide is stable at least at a temperature of about 10° C. to about 75° C.

5. A method for processing starch, comprising:
providing the thermophilic glucan phosphatase of claim 1;
exposing a starch to the thermophilic glucan phosphatase; and
collecting the starch that has been exposed to the thermophilic glucan phosphatase.

6. The method of claim 5, further comprising, before the collecting step, exposing the starch to a kinase, an amylase, or both.

* * * * *

SEQUENCE LISTING

```
<160> NUMBER OF SEQ ID NOS: 10

<210> SEQ ID NO 1
<211> LENGTH: 1599
<212> TYPE: DNA
<213> ORGANISM: Artificial Sequence
<220> FEATURE:
<223> OTHER INFORMATION: C. merolae laforin full-length

<400> SEQUENCE: 1
atggcgcgta tacgaacatc ggatcgccgg aacacaaacg accaggcagg ctcggaaagc      60
cggcatcggg tgccgtcgat ggcaagagcg ccagctgctg attcgtctgg tgcgcagtca     120
acaccagccg cacggcgtgc ttccgaggga gtctctgtag ctgagcctcc gtcaaagcca     180
gctgctgatt cgtctggtgc gcagtcaaca ccagccgcac ggcgtgcttc cgagggagtc     240
tctgtagctg ggcctccatc aaagccagct gccgattcgt ctggtgcgca gtcaacacca     300
gccgcacggt ttgcatccga gggtgtctct gtacctgagc ctccgtcaaa gccagctgct     360
gattcgtctg gtgcgcagtc aacaccagcc gcacggggtg cttccgagga tatctctgta     420
```

-continued

```
cctgggcctc cttcagacat tgcggacacg atctcaaaga atgatcgaag cgtaaccccg    480
acgattccga ctttattccg cgtctactgc cacacggagt ttggcgatgc tgtcgtcgcc    540
gctggtagtc acgacaaatt gggcaactgg gagcccgcga aagcgctccg gctccgtcat    600
caatgccaag tggatacacc gttccgtgac tgctgggaag gcgaggtaga ccttgtaccc    660
gaaacaagct tcgagttcaa attcgtgcgt cttataggcg agatccgca gcgtgcgctc    720
tgggaaaccg gacccaaccg aagagccgtg atccagagaa actcgaagga cggctgcctg    780
attgaagtgg aatgggagcg tacgcgtgtg ctgttctcaa tatactatcc taccaaagag    840
aagcagcatc tctgtgtcac tggcgatctt ccggaaatcg tcggtgggt agaaccgggt     900
ccagtaccca tggccctctc aactactgag gagcgtttgg aaacaggagg caagggccga    960
cgttggtcct tgacggtttc agtgccatcc acggtgggca aattcgccta tcgctatgtg   1020
ctagtcgacg ataaccgcca gcaaacgatc tgggaacgag aaccgaatcg ctatgcaaca   1080
ctagaacgag cggtgaacgg gcgcctcgaa tgtttcgatg caaattttgt cgcttcgtta   1140
gaatttgatg aaatatgtcc ggacatttac atagggccct acccacaaac tccagagcat   1200
gtcgaaatga tgcatgaggc ggggattacg gctgttttga atttacagac cgatgaggac   1260
tttgcacacc gcagtattcc ctggtcgacg ctgatggaga catatacagc actagagatg   1320
caagtcatcc gttgtccgat tccggatttt aatgcggagg cgctcatgca gttgcttccg   1380
gatgccgtac gcgctcttga tgcggcgctc aaggcgaagc gcgtcgtcta cgtgcactgt   1440
accgcaggaa tgggtcgagc gcccgctgta gttgtcgcct acctcgtgtg cgccgcggc    1500
atgacgctgg aggatgcctt gtcgcacgtt aaagcacgtc gtgctgtggc cgcgccgaat   1560
gtcaccgtat tggaaaaggt tcttcgtaat cccttgtga                          1599
```

<210> SEQ ID NO 2
<211> LENGTH: 532
<212> TYPE: PRT
<213> ORGANISM: Artificial Sequence
<220> FEATURE:
<223> OTHER INFORMATION: C. merolae laforin full-length polypeptide

<400> SEQUENCE: 2

```
Met Ala Arg Ile Arg Thr Ser Asp Arg Arg Asn Thr Asn Asp Gln Ala
1               5                   10                  15

Gly Ser Glu Ser Arg His Arg Val Pro Ser Met Ala Arg Ala Pro Ala
            20                  25                  30

Ala Asp Ser Ser Gly Ala Gln Ser Thr Pro Ala Ala Arg Arg Ala Ser
        35                  40                  45

Glu Gly Val Ser Val Ala Glu Pro Ser Lys Pro Ala Ala Asp Ser
    50                  55                  60

Ser Gly Ala Gln Ser Thr Pro Ala Ala Arg Arg Ala Ser Glu Gly Val
65                  70                  75                  80

Ser Val Ala Gly Pro Pro Ser Lys Pro Ala Ala Asp Ser Ser Gly Ala
                85                  90                  95

Gln Ser Thr Pro Ala Ala Arg Phe Ala Ser Glu Gly Val Ser Val Pro
            100                 105                 110

Glu Pro Pro Ser Lys Pro Ala Ala Asp Ser Ser Gly Ala Gln Ser Thr
        115                 120                 125

Pro Ala Ala Arg Gly Ala Ser Glu Asp Ile Ser Val Pro Gly Pro Pro
    130                 135                 140

Ser Asp Ile Ala Asp Thr Ile Ser Lys Asn Asp Arg Ser Val Thr Pro
```

```
            145                 150                 155                 160
        Thr Ile Pro Thr Leu Phe Arg Val Tyr Cys His Thr Glu Phe Gly Asp
                        165                 170                 175

Ala Val Ala Ala Gly Ser His Asp Lys Leu Gly Asn Trp Glu Pro
                    180                 185                 190

Ala Lys Ala Leu Arg Leu Arg His Gln Cys Gln Val Asp Thr Pro Phe
                        195                 200                 205

Arg Asp Cys Trp Glu Gly Glu Val Asp Leu Val Pro Glu Thr Ser Phe
                    210                 215                 220

Glu Phe Lys Phe Val Arg Leu Ile Gly Gly Asp Pro Gln Arg Ala Leu
        225                 230                 235                 240

Trp Glu Thr Gly Pro Asn Arg Arg Ala Val Ile Gln Arg Asn Ser Lys
                        245                 250                 255

Asp Gly Cys Leu Ile Glu Val Glu Trp Glu Arg Thr Arg Val Leu Phe
                        260                 265                 270

Ser Ile Tyr Tyr Pro Thr Lys Glu Lys Gln His Leu Cys Val Thr Gly
                    275                 280                 285

Asp Leu Pro Glu Ile Gly Arg Trp Val Glu Pro Gly Pro Val Pro Met
                    290                 295                 300

Ala Leu Ser Thr Thr Glu Glu Arg Leu Glu Thr Gly Gly Lys Gly Arg
        305                 310                 315                 320

Arg Trp Ser Leu Thr Val Ser Val Pro Ser Thr Val Gly Lys Phe Ala
                        325                 330                 335

Tyr Arg Tyr Val Leu Val Asp Asp Asn Arg Gln Gln Thr Ile Trp Glu
                    340                 345                 350

Arg Glu Pro Asn Arg Tyr Ala Thr Leu Glu Arg Ala Val Asn Gly Arg
                    355                 360                 365

Leu Glu Cys Phe Asp Ala Asn Phe Val Ala Ser Leu Glu Phe Asp Glu
                    370                 375                 380

Ile Cys Pro Asp Ile Tyr Ile Gly Pro Tyr Pro Gln Thr Pro Glu His
        385                 390                 395                 400

Val Glu Met Met His Glu Ala Gly Ile Thr Ala Val Leu Asn Leu Gln
                        405                 410                 415

Thr Asp Glu Asp Phe Ala His Arg Ser Ile Pro Trp Ser Thr Leu Met
                    420                 425                 430

Glu Thr Tyr Thr Ala Leu Glu Met Gln Val Ile Arg Cys Pro Ile Pro
                    435                 440                 445

Asp Phe Asn Ala Glu Ala Leu Met Gln Leu Leu Pro Asp Ala Val Arg
            450                 455                 460

Ala Leu Asp Ala Ala Leu Lys Ala Lys Arg Val Val Tyr Val His Cys
        465                 470                 475                 480

Thr Ala Gly Met Gly Arg Ala Pro Ala Val Val Ala Tyr Leu Val
                        485                 490                 495

Trp Arg Arg Gly Met Thr Leu Glu Asp Ala Leu Ser His Val Lys Ala
                    500                 505                 510

Arg Arg Ala Val Ala Ala Pro Asn Val Thr Val Leu Glu Lys Val Leu
                        515                 520                 525

Arg Asn Pro Leu
            530

<210> SEQ ID NO 3
<211> LENGTH: 1521
<212> TYPE: DNA
<213> ORGANISM: Artificial Sequence
```

```
<220> FEATURE:
<223> OTHER INFORMATION: C. merolae laforin Met 27 fragment

<400> SEQUENCE: 3
atggcaagag cgccagctgc tgattcgtct ggtgcgcagt caacaccagc cgcacggcgt      60
gcttccgagg gagtctctgt agctgagcct ccgtcaaagc cagctgctga ttcgtctggt     120
gcgcagtcaa caccagccgc acggcgtgct ccgagggag tctctgtagc tgggcctcca      180
tcaaagccag ctgccgattc gtctggtgcg cagtcaacac cagccgcacg gtttgcatcc     240
gagggtgtct ctgtacctga gcctccgtca aagccagctg ctgattcgtc tggtgcgcag     300
tcaacaccag ccgcacgggg tgcttccgag gatatctctg tacctgggcc tccttcagac     360
attgcggaca cgatctcaaa gaatgatcga agcgtaaccc cgacgattcc gactttattc     420
cgcgtctact gccacacgga gtttggcgat gctgtcgtcg ccgctggtag tcacgacaaa     480
ttgggcaact gggagcccgc gaaagcgctc cggctccgtc atcaatgcca agtggataca     540
ccgttccgtg actgctggga aggcgaggta gaccttgtac cgaaacaag cttcgagttc      600
aaattcgtgc gtcttatagg cggagatccg cagcgtgcgc tctgggaaac cggacccaac     660
cgaagagccg tgatccagag aaactcgaag gacggctgcc tgattgaagt ggaatgggag     720
cgtacgcgtg tgctgttctc aatatactat cctaccaaag agaagcagca tctctgtgtc     780
actggcgatc ttccggaaat cggtcggtgg gtagaaccgg gtccagtacc catggccctc     840
tcaactactg aggagcgttt ggaaacagga ggcaagggcc gacgttggtc cttgacggtt     900
tcagtgccat ccacggtggg caaattcgcc tatcgctatg tgctagtcga cgataaccgc     960
cagcaaacga tctgggaacg agaaccgaat cgctatgcaa cactagaacg agcggtgaac    1020
gggcgcctcg aatgtttcga tgcaaatttt gtcgcttcgt tagaatttga tgaaatatgt    1080
ccggacattt acatagggcc ctacccacaa actccagagc atgtcgaaat gatgcatgag    1140
gcggggatta cggctgtttt gaatttacag accgatgagg actttgcaca ccgcagtatt    1200
ccctggtcga cgctgatgga gacatataca gcactagaga tgcaagtcat ccgttgtccg    1260
attccggatt ttaatgcgga ggcgctcatg cagttgcttc cggatgccgt acgcgctctt    1320
gatgcggcgc tcaaggcgaa gcgcgtcgtc tacgtgcact gtaccgcagg aatgggtcga    1380
gcgcccgctg tagttgtcgc ctacctcgtg tggcgccgcg gcatgacgct ggaggatgcc    1440
ttgtcgcacg ttaaagcacg tcgtgctgtg ccgcgccga atgtcaccgt attggaaaag    1500
gttcttcgta atcccttgtg a                                              1521

<210> SEQ ID NO 4
<211> LENGTH: 506
<212> TYPE: PRT
<213> ORGANISM: Artificial Sequence
<220> FEATURE:
<223> OTHER INFORMATION: C. merolae laforin Met 27 polypeptide

<400> SEQUENCE: 4

Met Ala Arg Ala Pro Ala Ala Asp Ser Ser Gly Ala Gln Ser Thr Pro
1               5                   10                  15

Ala Ala Arg Arg Ala Ser Glu Gly Val Ser Val Ala Glu Pro Pro Ser
            20                  25                  30

Lys Pro Ala Ala Asp Ser Ser Gly Ala Gln Ser Thr Pro Ala Ala Arg
        35                  40                  45

Arg Ala Ser Glu Gly Val Ser Val Ala Gly Pro Pro Ser Lys Pro Ala
    50                  55                  60
```

```
Ala Asp Ser Ser Gly Ala Gln Ser Thr Pro Ala Arg Phe Ala Ser
 65                  70                  75                  80

Glu Gly Val Ser Val Pro Glu Pro Pro Ser Lys Pro Ala Ala Asp Ser
                 85                  90                  95

Ser Gly Ala Gln Ser Thr Pro Ala Ala Arg Gly Ala Ser Glu Asp Ile
            100                 105                 110

Ser Val Pro Gly Pro Pro Ser Asp Ile Ala Asp Thr Ile Ser Lys Asn
        115                 120                 125

Asp Arg Ser Val Thr Pro Thr Ile Pro Thr Leu Phe Arg Val Tyr Cys
    130                 135                 140

His Thr Glu Phe Gly Asp Ala Val Val Ala Ala Gly Ser His Asp Lys
145                 150                 155                 160

Leu Gly Asn Trp Glu Pro Ala Lys Ala Leu Arg Leu Arg His Gln Cys
                165                 170                 175

Gln Val Asp Thr Pro Phe Arg Asp Cys Trp Glu Gly Val Asp Leu
            180                 185                 190

Val Pro Glu Thr Ser Phe Glu Phe Lys Phe Val Arg Leu Ile Gly Gly
        195                 200                 205

Asp Pro Gln Arg Ala Leu Trp Glu Thr Gly Pro Asn Arg Arg Ala Val
    210                 215                 220

Ile Gln Arg Asn Ser Lys Asp Gly Cys Leu Ile Glu Val Glu Trp Glu
225                 230                 235                 240

Arg Thr Arg Val Leu Phe Ser Ile Tyr Tyr Pro Thr Lys Glu Lys Gln
                245                 250                 255

His Leu Cys Val Thr Gly Asp Leu Pro Glu Ile Gly Arg Trp Val Glu
            260                 265                 270

Pro Gly Pro Val Pro Met Ala Leu Ser Thr Thr Glu Glu Arg Leu Glu
        275                 280                 285

Thr Gly Gly Lys Gly Arg Arg Trp Ser Leu Thr Val Ser Val Pro Ser
    290                 295                 300

Thr Val Gly Lys Phe Ala Tyr Arg Tyr Val Leu Val Asp Asp Asn Arg
305                 310                 315                 320

Gln Gln Thr Ile Trp Glu Arg Glu Pro Asn Arg Tyr Ala Thr Leu Glu
                325                 330                 335

Arg Ala Val Asn Gly Arg Leu Glu Cys Phe Asp Ala Asn Phe Val Ala
            340                 345                 350

Ser Leu Glu Phe Asp Glu Ile Cys Pro Asp Ile Tyr Ile Gly Pro Tyr
        355                 360                 365

Pro Gln Thr Pro Glu His Val Glu Met Met His Glu Ala Gly Ile Thr
    370                 375                 380

Ala Val Leu Asn Leu Gln Thr Asp Glu Asp Phe Ala His Arg Ser Ile
385                 390                 395                 400

Pro Trp Ser Thr Leu Met Glu Thr Tyr Thr Ala Leu Glu Met Gln Val
                405                 410                 415

Ile Arg Cys Pro Ile Pro Asp Phe Asn Ala Glu Ala Leu Met Gln Leu
            420                 425                 430

Leu Pro Asp Ala Val Arg Ala Leu Asp Ala Ala Leu Lys Ala Lys Arg
        435                 440                 445

Val Val Tyr Val His Cys Thr Ala Gly Met Gly Arg Ala Pro Ala Val
    450                 455                 460

Val Val Ala Tyr Leu Val Trp Arg Arg Gly Met Thr Leu Glu Asp Ala
465                 470                 475                 480

Leu Ser His Val Lys Ala Arg Arg Ala Val Ala Ala Pro Asn Val Thr
```

Val Leu Glu Lys Val Leu Arg Asn Pro Leu
            500                 505

<210> SEQ ID NO 5
<211> LENGTH: 1140
<212> TYPE: DNA
<213> ORGANISM: Artificial Sequence
<220> FEATURE:
<223> OTHER INFORMATION: C. merolae laforin Ser157 fragment polypeptide

<400> SEQUENCE: 5

```
atgtcagtta ccccgaccat cccgacgctg ttccgtgttt attgtcacac cgaatttggc      60
gacgcagttg ttgccgctgg ctcccatgat aaactgggta actgggaacc ggcaaaagct     120
ctgcgtctgc gccatcagtg ccaagttgat acccgttcc gtgactgttg gaaggcgaa      180
gtggatctgg ttccggaaac gagttttgaa tttaaattcg tccgtctgat tggcggtgac     240
ccgcagcgcg cactgtggga accggtccg aaccgtcgcg ctgtgattca acgcaatagc      300
aaagatggct gcctgatcga agttaatgg gaacgtacgc gcgtcctgtt ttctatctac      360
tacccgacca agaaaaaaca gcacctgtgt gttacgggcg acctgccgga atcggtcgt      420
tgggtcgaac cgggtccggt gccgatggcg ctgtcaacca cggaagaacg cctggaaacc     480
ggcggtaaag tcgtcgctg tcgctgacc gtcagcgtgc cgtctacggt gggcaaattc      540
gcctatcgtt acgttctggt cgatgacaac cgccagcaaa ccatttggga acgtgaaccg     600
aatcgctatg caacgctgga acgtgctgtc aacggtcgcc tggaatgctt cgatgcaaat     660
tttgtggctt ccctggaatt tgatgaaatc tgtccggaca tttatatcgg tccgtacccg     720
cagaccccgg aacatgtgga aatgatgcac gaagcgggca ttaccgccgt tctgaacctg     780
caaacggatg aagacttcgc ccatcgtagt atcccgtggt ccaccctgat ggaaacctac     840
acggcactgg aaatgcaagt gattcgctgc ccgatcccgg attttaatgc ggaagccctg     900
atgcaactgc tgccggatgc agtgcgtgcc ctggacgcag ccctgaaagc aaaacgcgtg     960
gtttatgttc attgtaccgc gggcatgggt cgtgcaccgg ctgtcgtggt tgcgtacctg    1020
gtttggcgtc gcggcatgac gctggaagat gcgctgagcc acgtcaaagc ccgccgtgct    1080
gttgccgccc cgaatgtgac ggtgctggaa aaagttctgc gtaacccgct gtaactcgag    1140
```

<210> SEQ ID NO 6
<211> LENGTH: 377
<212> TYPE: PRT
<213> ORGANISM: Artificial Sequence
<220> FEATURE:
<223> OTHER INFORMATION: C. merolae laforin Ser157 fragment polypeptide

<400> SEQUENCE: 6

Met Ser Val Thr Pro Thr Ile Pro Thr Leu Phe Arg Val Tyr Cys His
1               5                   10                  15

Thr Glu Phe Gly Asp Ala Val Val Ala Ala Gly Ser His Asp Lys Leu
            20                  25                  30

Gly Asn Trp Glu Pro Ala Lys Ala Leu Arg Leu Arg His Gln Cys Gln
        35                  40                  45

Val Asp Thr Pro Phe Arg Asp Cys Trp Glu Gly Glu Val Asp Leu Val
    50                  55                  60

Pro Glu Thr Ser Phe Glu Phe Lys Phe Val Arg Leu Ile Gly Gly Asp
65                  70                  75                  80

Pro Gln Arg Ala Leu Trp Glu Thr Gly Pro Asn Arg Arg Ala Val Ile

|  |  |  | 85 |  |  |  | 90 |  |  |  | 95 |  |
|---|---|---|---|---|---|---|---|---|---|---|---|---|

Gln Arg Asn Ser Lys Asp Gly Cys Leu Ile Glu Val Glu Trp Glu Arg
                      100                              105                      110

Thr Arg Val Leu Phe Ser Ile Tyr Tyr Pro Thr Lys Glu Lys Gln His
                      115                              120                      125

Leu Cys Val Thr Gly Asp Leu Pro Glu Ile Gly Arg Trp Val Glu Pro
130                              135                              140

Gly Pro Val Pro Met Ala Leu Ser Thr Glu Glu Arg Leu Glu Thr
145                         150                            155                        160

Gly Gly Lys Gly Arg Arg Trp Ser Leu Thr Val Ser Val Pro Ser Thr
                      165                              170                      175

Val Gly Lys Phe Ala Tyr Arg Tyr Val Leu Val Asp Asp Asn Arg Gln
                      180                              185                      190

Gln Thr Ile Trp Glu Arg Glu Pro Asn Arg Tyr Ala Thr Leu Glu Arg
                      195                              200                      205

Ala Val Asn Gly Arg Leu Glu Cys Phe Asp Ala Asn Phe Val Ala Ser
    210                            215                              220

Leu Glu Phe Asp Glu Ile Cys Pro Asp Ile Tyr Ile Gly Pro Tyr Pro
225                              230                              235                      240

Gln Thr Pro Glu His Val Glu Met Met His Glu Ala Gly Ile Thr Ala
                      245                              250                      255

Val Leu Asn Leu Gln Thr Asp Glu Asp Phe Ala His Arg Ser Ile Pro
    260                            265                              270

Trp Ser Thr Leu Met Glu Thr Tyr Thr Ala Leu Glu Met Gln Val Ile
        275                          280                            285

Arg Cys Pro Ile Pro Asp Phe Asn Ala Glu Ala Leu Met Gln Leu Leu
    290                            295                            300

Pro Asp Ala Val Arg Ala Leu Asp Ala Ala Leu Lys Ala Lys Arg Val
305                              310                              315                      320

Val Tyr Val His Cys Thr Ala Gly Met Gly Arg Ala Pro Ala Val Val
                      325                              330                      335

Val Ala Tyr Leu Val Trp Arg Arg Gly Met Thr Leu Glu Asp Ala Leu
                      340                              345                      350

Ser His Val Lys Ala Arg Arg Ala Val Ala Ala Pro Asn Val Thr Val
    355                            360                              365

Leu Glu Lys Val Leu Arg Asn Pro Leu
    370                            375

<210> SEQ ID NO 7
<211> LENGTH: 831
<212> TYPE: DNA
<213> ORGANISM: Artificial Sequence
<220> FEATURE:
<223> OTHER INFORMATION: C. merolae laforin Gly258 fragment

<400> SEQUENCE: 7

| | | | |
|---|---|---|---|
| atgggctgcc tgatcgaagt tgaatgggaa cgtacgcgcg tcctgttttc tatctactac | | | 60 |
| ccgaccaaag aaaaacagca cctgtgtgtt acgggcgacc tgccggaaat cggtcgttgg | | | 120 |
| gtcgaaccgg gtccggtgcc gatggcgctg tcaaccacgg aagaacgcct ggaaaccggc | | | 180 |
| ggtaaaggtc gtcgctggtc gctgaccgtc agcgtgccgt ctacggtggg caaattcgcc | | | 240 |
| tatcgttacg ttctggtcga tgacaaccgc cagcaaacca tttgggaacg tgaaccgaat | | | 300 |
| cgctatgcaa cgctggaacg tgctgtcaac ggtcgcctgg aatgcttcga tgcaaatttt | | | 360 |
| gtggcttccc tggaatttga tgaaatctgt ccggacattt atatcggtcc gtaccgcag | | | 420 |

```
acccccggaac atgtggaaat gatgcacgaa gcgggcatta ccgccgttct gaacctgcaa    480
acggatgaag acttcgccca tcgtagtatc ccgtggtcca ccctgatgga aacctacacg    540
gcactggaaa tgcaagtgat tcgctgcccg atcccggatt taatgcgga agccctgatg    600 caactgctgc cggatgcagt gcgtgccctg gacgcagccc tgaaagcaaa acgcgtggtt    660
tatgttcatt gtaccgcggg catgggtcgt gcaccggctg tcgtggttgc gtacctggtt    720
tggcgtcgcg gcatgacgct ggaagatgcg ctgagccacg tcaaagcccg ccgtgctgtt    780
gccgccccga atgtgacggg gctggaaaaa gttctgcgta acccgctgta a              831
```

<210> SEQ ID NO 8
<211> LENGTH: 276
<212> TYPE: PRT
<213> ORGANISM: Artificial Sequence
<220> FEATURE:
<223> OTHER INFORMATION: C. merolae laforin Gly258 fragment polypeptide

<400> SEQUENCE: 8

```
Met Gly Cys Leu Ile Glu Val Glu Trp Glu Arg Thr Arg Val Leu Phe
1               5                   10                  15

Ser Ile Tyr Tyr Pro Thr Lys Glu Lys Gln His Leu Cys Val Thr Gly
            20                  25                  30

Asp Leu Pro Glu Ile Gly Arg Trp Val Glu Pro Gly Pro Val Pro Met
        35                  40                  45

Ala Leu Ser Thr Thr Glu Glu Arg Leu Glu Thr Gly Gly Lys Gly Arg
    50                  55                  60

Arg Trp Ser Leu Thr Val Ser Val Pro Ser Thr Val Gly Lys Phe Ala
65                  70                  75                  80

Tyr Arg Tyr Val Leu Val Asp Asp Asn Arg Gln Gln Thr Ile Trp Glu
                85                  90                  95

Arg Glu Pro Asn Arg Tyr Ala Thr Leu Glu Arg Ala Val Asn Gly Arg
            100                 105                 110

Leu Glu Cys Phe Asp Ala Asn Phe Val Ala Ser Leu Glu Phe Asp Glu
        115                 120                 125

Ile Cys Pro Asp Ile Tyr Ile Gly Pro Tyr Pro Gln Thr Pro Glu His
    130                 135                 140

Val Glu Met Met His Glu Ala Gly Ile Thr Ala Val Leu Asn Leu Gln
145                 150                 155                 160

Thr Asp Glu Asp Phe Ala His Arg Ser Ile Pro Trp Ser Thr Leu Met
                165                 170                 175

Glu Thr Tyr Thr Ala Leu Glu Met Gln Val Ile Arg Cys Pro Ile Pro
            180                 185                 190

Asp Phe Asn Ala Glu Ala Leu Met Gln Leu Leu Pro Asp Ala Val Arg
        195                 200                 205

Ala Leu Asp Ala Ala Leu Lys Ala Lys Arg Val Val Tyr Val His Cys
    210                 215                 220

Thr Ala Gly Met Gly Arg Ala Pro Ala Val Val Ala Tyr Leu Val
225                 230                 235                 240

Trp Arg Arg Gly Met Thr Leu Glu Asp Ala Leu Ser His Val Lys Ala
                245                 250                 255

Arg Arg Ala Val Ala Ala Pro Asn Val Thr Val Leu Glu Lys Val Leu
            260                 265                 270

Arg Asn Pro Leu
        275
```

<210> SEQ ID NO 9
<211> LENGTH: 801
<212> TYPE: DNA
<213> ORGANISM: Artificial Sequence
<220> FEATURE:
<223> OTHER INFORMATION: C. merolae laforin Arg267 fragment

<400> SEQUENCE: 9

```
cgtacgcgcg tcctgttttc tatctactac ccgaccaaag aaaaacagca cctgtgtgtt      60
acgggcgacc tgccggaaat cggtcgttgg gtcgaaccgg gtccggtgcc gatggcgctg     120
tcaaccacgg aagaacgcct ggaaaccggc ggtaaaggtc gtcgctggtc gctgaccgtc     180
agcgtgccgt ctacggtggg caaattcgcc tatcgttacg ttctggtcga tgacaaccgc     240
cagcaaacca tttgggaacg tgaaccgaat cgctatgcaa cgctggaacg tgctgtcaac     300
ggtcgcctgg aatgcttcga tgcaaatttt gtggcttccc tggaatttga tgaaatctgt     360
ccggacattt atatcggtcc gtacccgcag accccggaac atgtggaaat gatgcacgaa     420
gcgggcatta ccgccgttct gaacctgcaa acggatgaag acttcgccca tcgtagtatc     480
ccgtggtcca ccctgatgga aacctacacg gcactggaaa tgcaagtgat tcgctgcccg     540
atcccggatt ttaatgcgga agccctgatg caactgctgc cggatgcagt gcgtgccctg     600
gacgcagccc tgaaagcaaa acgcgtggtt tatgttcatt gtaccgcggg catgggtcgt     660
gcaccggctg tcgtggttgc gtacctggtt tggcgtcgcg gcatgacgct ggaagatgcg     720
ctgagccacg tcaaagcccg ccgtgctgtt gccgccccga atgtgacggt gctggaaaaa     780
gttctgcgta acccgctgta a                                               801
```

<210> SEQ ID NO 10
<211> LENGTH: 267
<212> TYPE: PRT
<213> ORGANISM: Artificial Sequence
<220> FEATURE:
<223> OTHER INFORMATION: C. merolae laforin Arg267 fragment polypeptide

<400> SEQUENCE: 10

Met Arg Thr Arg Val Leu Phe Ser Ile Tyr Tyr Pro Thr Lys Glu Lys
1               5                   10                  15

Gln His Leu Cys Val Thr Gly Asp Leu Pro Glu Ile Gly Arg Trp Val
            20                  25                  30

Glu Pro Gly Pro Val Pro Met Ala Leu Ser Thr Thr Glu Glu Arg Leu
        35                  40                  45

Glu Thr Gly Gly Lys Gly Arg Arg Trp Ser Leu Thr Val Ser Val Pro
    50                  55                  60

Ser Thr Val Gly Lys Phe Ala Tyr Arg Tyr Val Leu Val Asp Asp Asn
65                  70                  75                  80

Arg Gln Gln Thr Ile Trp Glu Arg Glu Pro Asn Arg Tyr Ala Thr Leu
                85                  90                  95

Glu Arg Ala Val Asn Gly Arg Leu Glu Cys Phe Asp Ala Asn Phe Val
            100                 105                 110

Ala Ser Leu Glu Phe Asp Glu Ile Cys Pro Asp Ile Tyr Ile Gly Pro
        115                 120                 125

Tyr Pro Gln Thr Pro Glu His Val Glu Met Met His Glu Ala Gly Ile
    130                 135                 140

Thr Ala Val Leu Asn Leu Gln Thr Asp Glu Asp Phe Ala His Arg Ser
145                 150                 155                 160

Ile Pro Trp Ser Thr Leu Met Glu Thr Tyr Thr Ala Leu Glu Met Gln

-continued

```
                165                 170                 175
Val Ile Arg Cys Pro Ile Pro Asp Phe Asn Ala Glu Ala Leu Met Gln
            180                 185                 190

Leu Leu Pro Asp Ala Val Arg Ala Leu Asp Ala Ala Leu Lys Ala Lys
        195                 200                 205

Arg Val Val Tyr Val His Cys Thr Ala Gly Met Gly Arg Ala Pro Ala
    210                 215                 220

Val Val Val Ala Tyr Leu Val Trp Arg Arg Gly Met Thr Leu Glu Asp
225                 230                 235                 240

Ala Leu Ser His Val Lys Ala Arg Arg Ala Val Ala Ala Pro Asn Val
            245                 250                 255

Thr Val Leu Glu Lys Val Leu Arg Asn Pro Leu
            260                 265
```